US00PP07794P

United States Patent [19]

Drewlow

[11] Patent Number: Plant 7,794

[45] Date of Patent: Feb. 18, 1992

[54] KALANCHOE PLANT NAMED MAJESTIC

[75] Inventor: Lyndon W. Drewlow, Ashtabula, Ohio

[73] Assignee: Mikkelsens, Inc., Ashtabula, Ohio

[21] Appl. No.: 607,377

[22] Filed: Oct. 31, 1990

[51] Int. Cl.[5] ..... A01H 5/00
[52] U.S. Cl. ..... Plt./68
[58] Field of Search ..... Plt./68

*Primary Examiner*—James R. Feyrer
*Attorney, Agent, or Firm*—Foley & Lardner

[57] ABSTRACT

A new and distinct cultivar of Kalanchoe plant named Majestic, characterized particularly by its large, scarlet colors, excellent flower keeping qualities, mounded growth habit with flowers being above the foliage, and by its floriferous habit.

1 Drawing Sheet

The present invention relates to a new and distinctive cultivar Kalanchoe plant, botanically known as Kalanchoe, and known by the cultivar name Majestic. Majestic was discovered by me through controlled breeding by crossing Mikkelsen Seedling No. 84-2848-2 (seed parent) with Attraction (pollen parent). Attraction is disclosed in U.S. Plant Pat. No. 5,888.

Asexual reproduction by stem cuttings has shown that the unique features of Majestic are stabilized and are reproduced true to type in successive propagations.

The following characteristics distinguish Majestic from both its parent varieties and other cultivated Kalanchoes of this type known and used in the floriculture industry, including the comparison cultivar Royalty, disclosed in U.S. Plant Pat. No. 5,254. Color references are to the Royal Horticultural Society Colour Chart (R.H.S.).

1. Majestic has scarlet rose (45B) flowers that contain more anthocyanin pigment than the flowers of Royalty which are rose (51A) with a small amount of anthocyanin pigment.

2. Flowering time for Majestic is 4 to 7 days earlier than Royalty under summer conditions, and 10 to 14 days earlier under winter growing conditions, from start of short day treatment.

3. Average flower diameter of Majestic is 15 to 16 mm while Royalty has a much smaller average flower diameter of 12 to 13 mm.

4. Average height of Majestic is 18 to 20 cm while Royalty is 22 to 24 cm high when grown under similar conditions.

5. Keeping quality of individual flowers of Majestic is three to five days longer than Royalty, and the length of time plants of Majestic will continue to flower after short day treatment is one to two weeks longer than for Royalty.

6. The leaf color and size of both Royalty and Majestic are similar. However, Royalty has deeper cut crenations than Majestic and there is more lobing to the Royalty leaf.

7. Internodes, peduncles and pedicels are shorter on Majestic than Royalty, thus giving the overall plant of Majestic a more dense appearance. The total inflorescence of Majestic presents a solid mass of flowers without openings.

8. The lower branches of Majestic tend to grow outward and not as long as the main stem and upper branches, thereby presenting a mounded appearance. All branches and the main stem of Royalty finish at the same height resulting in an upright growing plant with flowers at the top.

9. Mature stigmas on Royalty are white with a reddish cast, while Majestic has white mature stigmas.

The accompanying colored photograph illustrates in front perspective view the overall appearance of Majestic, showing the colors as true as it is reasonably possible to obtain in a colored reproduction of this type. The photograph was taken on Mar. 23, 1990 under natural light on an overcast day, under double poly greenhouse covering at Ashtabula, Ohio.

The following is a detailed description of Majestic, based on plants produced in greenhouses in Ashtabula, Ohio during the late spring to summer season of the year. Plants were grown in 10 cm pots and measurements were taken 12 weeks after rooted cuttings were planted. Height measurements were taken from the soil line of the container. The plants were grown at 65°–68° F. night temperatures, under 3500–4000 foot candles of light, and 240 ppm nitrogen, 240 ppm potassium, and 175 ppm phosphorous nutritional levels with trace elements added. 5000 ppm B-9 was applied week three and week five of short day treatment of the six week short day treatment (14 hours dark) period. Habit of growth, plant height, flowering time, size of leaves and peduncle length will be greatly influenced by nutritional and environmental conditions.

Colors references are made to the Royal Horticultural Society Colour Chart except where general terms of ordinary dictionary significance are used.

Parentage: A controlled cross between female parent Mikkelsen Seedling No. 84-2848-2 and male parent Attraction.

Propagation:

(A) *Type cutting.*—Stem tip cutting up to 3 cm long.

(B) *Time to root.*—10 days at 21° C. in summer; 14 days at 21° C. in winter.

(C) *Rooting habit.*—Abundant, fine, fibrous roots.

Plant description:

(A) *Habit and form of growth.*—Compact; flower clusters are held above foliage; excellent basal branching results in mounded growth habit. Environment and use of growth regulators will play a role in final height.

(B) *Foliage description.*—Leaves simple and opposite. 1. Size: Average; full grown leaves on a plant when grown in a 10 cm pot are 10 to 11 cm long and 5.5 to 6.0 cm wide. 2. Shape: Ovate; apex obtuse, base rounded. 3. Texture: Glabrous, coriaceous, and succulent. 4. Margin: Crenate; shallow lobed. 5. Color: Young foliage, top side 137B; under side 146B; mature foliage, top side 147A; underside 147B.

Flowering description:

(A) *Flowering habits.*—Inflorescence is a cyme. Terminal flower on main axis opens first, followed by the terminal flowers of the side branches, continuing with the subsequent development of branches in the inflorescence. Inflorescence is made up of the main stem and up to ten or more lateral branches.

(B) *Natural flowering season.*—Early January. Flowering time under controlled daylength at 20° C. in summer is 10 weeks; in winter 11½ weeks. Flowering time depends on temperature, light intensity and other growing conditions.

(C) *Flower buds.*—Oblong, up to 7 mm long before showing color, developing tubular as flower petals mature; sheathed in four green sepals.

(D) *Flowers borne.*—On compound dichasial cymes, primary peduncle 4 mm in diameter just below the first branch of the inflorescence; length will vary depending on growing conditions. Pedicels vary in length depending on where they are located in the inflorescence.

(E) *Quantity of flowers.*—Very floriferous with main stem plus 10 or more laterals each having from 30 to 50 flowers.

(F) *Petals.*—1. Shape: Almost rounded, top cuspidate. 2. Color, top side when opening: 45B fading to 45C to 45D; under side 47D. 3. Number of petals: Four. 4. Size: Individual petals 6 mm wide and 8 mm long; flowers 15 mm in diameter.

Reproductive organs:

1. *Stamens.*—Number, 8. a. Anther shape: Flat, elliptical; color yellowish green. b. Filament color: Light green. c. Pollen color: Yellow.
2. *Pistils.*—a. Stigma shape: Flat; mature color, whitish. b. Style color: Green. c. Ovaries: Four, size 6 mm, color green.

Disease resistance: Majestic has shown resistance to Powdery Mildew and no other disease problems have been noted to date.

Other important characteristics: Majestic is part of a series of Kalanchoe plants that include Revelry, Splendor, Keepsake and Heirloom (all disclosed in pending plant patent applications of applicant) that are similar in flowering time, height, branching and response to growth regulators. This allows the greenhouse growers to handle all five distinctly different flower colors at the same time from a single planting date and use the same growing methods on each to end up with a uniform crop. The end results are easier crops for the growers to produce and higher quality crops. All cultivars are ideal for 10 and 15 cm pot production.

I claim:

1. A new and distinct cultivar of Kalanchoe plant named Majestic, as illustrated and described.

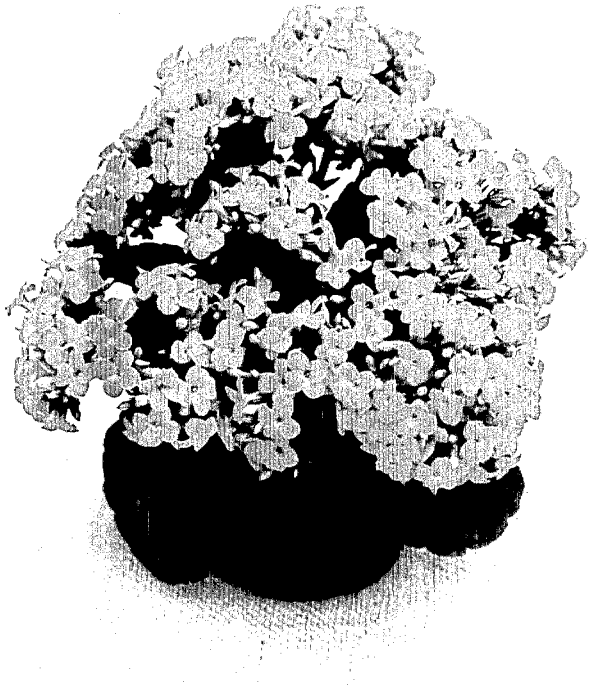

* * * * *